US012679797B2

(12) United States Patent
Kuo et al.

(10) Patent No.: US 12,679,797 B2
(45) Date of Patent: Jul. 14, 2026

(54) COMPOSITION AND METHOD FOR PREPARING THE SAME

(71) Applicant: INDUSTRIAL TECHNOLOGY RESEARCH INSTITUTE, Hsinchu (TW)

(72) Inventors: Shin-Liang Kuo, Hsinchu City (TW); Yu-Lan Tung, Hsinchu City (TW); Wen-Sheng Chang, Zaoqiao Township (TW); Kung-Hsun Huang, Hsinchu City (TW); Tein-San Lee, Zhubei City (TW); Shu-Chuan Huang, Zhubei City (TW)

(73) Assignee: INDUSTRIAL TECHNOLOGY RESEARCH INSTITUTE, Hsinchu (TW)

( * ) Notice: Subject to any disclaimer, the term of this patent is extended or adjusted under 35 U.S.C. 154(b) by 682 days.

(21) Appl. No.: 18/148,648

(22) Filed: Dec. 30, 2022

(65) Prior Publication Data

US 2024/0228421 A1 Jul. 11, 2024

(51) Int. Cl.
*C07C 67/02* (2006.01)
*B01J 21/06* (2006.01)
(Continued)

(52) U.S. Cl.
CPC ............ *C07C 67/02* (2013.01); *B01J 21/063* (2013.01); *B01J 23/06* (2013.01); *C07C 67/56* (2013.01);
(Continued)

(58) Field of Classification Search
CPC ......... C07C 67/02; C07C 67/03; C07C 69/82; C08J 11/24; C08J 2387/02; B01J 23/02;
(Continued)

(56) References Cited

U.S. PATENT DOCUMENTS 7,030,264 B1 4/2006 Inada et al.
7,211,193 B2 5/2007 Inada et al.
(Continued)

FOREIGN PATENT DOCUMENTS

CN 107189044 A * 9/2017 ............... B29B 9/12
CN 110590551 A 12/2019
(Continued)

OTHER PUBLICATIONS

Xi, et al., Study on depolymerization of waste polyethylene terephthalate into monomer of bis(2-hydroxyethyl terephthalate), Polymer Degradation and Stability, vol. 87, No. 1, pp. 117-120 (Year: 2005).*
(Continued)

*Primary Examiner* — Yate' K Cutliff
(74) *Attorney, Agent, or Firm* — Birch, Stewart, Kolasch & Birch, LLP

(57) ABSTRACT

A composition and a method for preparing the same are provided. The method for preparing the composition includes providing a polyethylene terephthalate waste. The polyethylene terephthalate waste is subjected to a depolymerization in the presence of a catalyst and an alcoholysis agent to obtain a mixture, wherein an oxidizing atmosphere is continuously introduced into the depolymerization. The mixture is subjected to a solid-liquid separation to obtain a solid. The solid is subjected to a purification to obtain the composition.

12 Claims, 1 Drawing Sheet

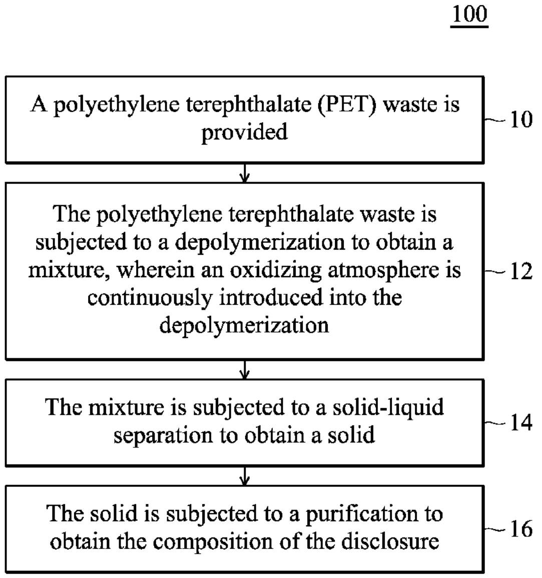

(51) Int. Cl.
*B01J 23/06* (2006.01)
*C07C 67/56* (2006.01)
*C07C 69/82* (2006.01)
*C08J 11/24* (2006.01)

(52) U.S. Cl.
CPC ............... *C07C 69/82* (2013.01); *C08J 11/24* (2013.01); *C08J 2367/02* (2013.01)

(58) Field of Classification Search
CPC ... B01J 23/06; B01J 23/34; B01J 23/54; B01J 21/063
See application file for complete search history.

(56) References Cited

U.S. PATENT DOCUMENTS

| | | | | |
|---|---|---|---|---|
| 9,127,136 | B1 * | 9/2015 | Bell | C07C 67/56 |
| 2021/0047495 | A1 | 2/2021 | Parrott | |
| 2022/0056202 | A1 | 2/2022 | Vollenberg et al. | |

FOREIGN PATENT DOCUMENTS

| | | | | | |
|---|---|---|---|---|---|
| CN | 109574835 | B | | 1/2021 | |
| CN | 112406148 | A | * | 2/2021 | B29B 9/12 |
| CN | 112898155 | A | | 6/2021 | |
| CZ | 299908 | B6 | * | 12/2008 | C08J 11/10 |
| JP | 2006-232701 | A | | 9/2006 | |
| TW | 506968 | B | | 10/2002 | |
| WO | WO 2021/124149 | A1 | | 6/2021 | |
| WO | WO 2022/004359 | A1 | | 1/2022 | |
| WO | WO-2022243832 | A1 | * | 11/2022 | C08J 11/24 |

OTHER PUBLICATIONS

Taiwanese Office Action and Search Report for Taiwanese Application No. 112111082, dated Oct. 26, 2023.

Huang et al., "Ion-Exchange Resins for Efficient Removal of Colorants in Bis(hydroxyethyl) Terephthalate", ACS Omega, Apr. 29, 2021, vol. 6, No. 18, pp. 12351-12360.

Huang et al., "Removal of trace amount impurities in glycolytic monomer of polyethylene terephthalate by recrystallization", Elsevier, Journal of Environmental Chemical Engineering, Oct. 2021, vol. 9, Issue 5, 106277, pp. 1-8.

* cited by examiner

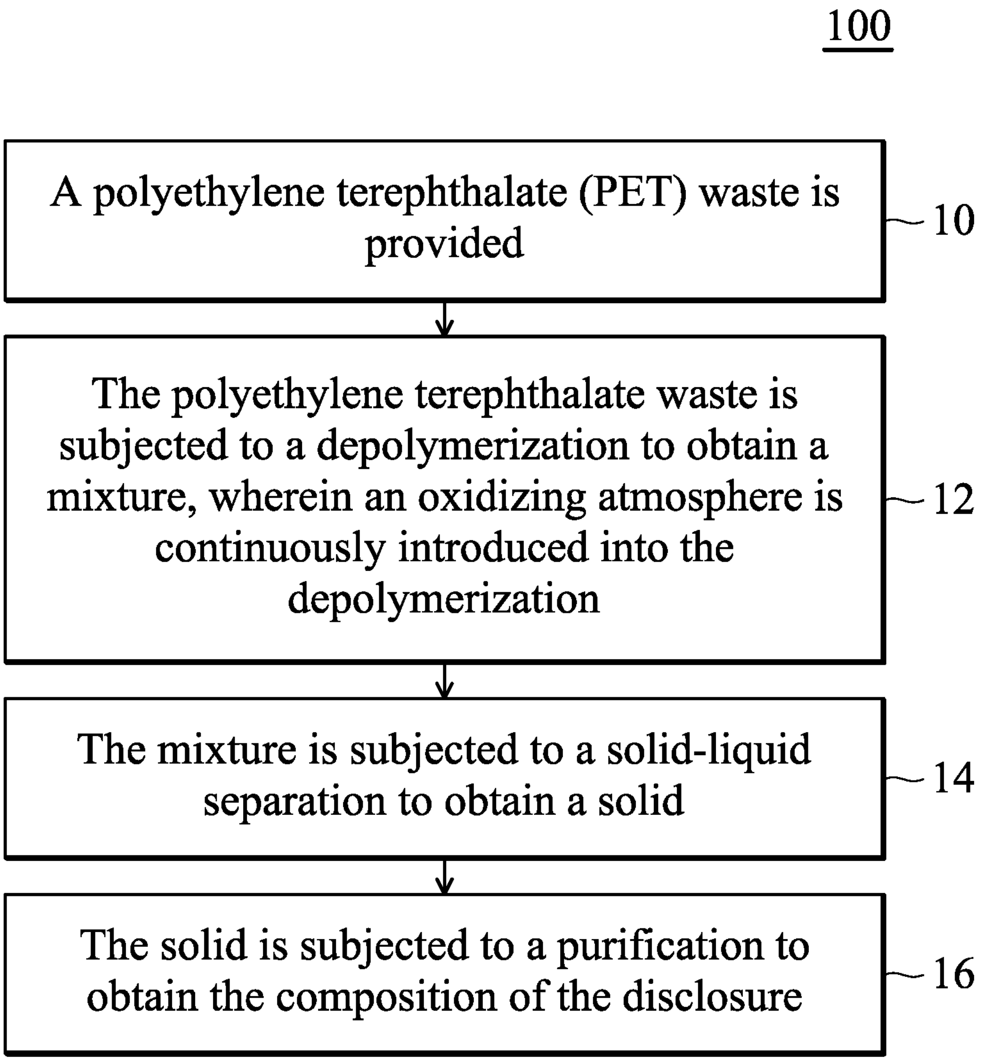
100
A polyethylene terephthalate (PET) waste is provided
10
The polyethylene terephthalate waste is subjected to a depolymerization to obtain a mixture, wherein an oxidizing atmosphere is continuously introduced into the depolymerization
12
The mixture is subjected to a solid-liquid separation to obtain a solid
14
The solid is subjected to a purification to obtain the composition of the disclosure
16

COMPOSITION AND METHOD FOR PREPARING THE SAME

TECHNICAL FIELD

The disclosure relates to a composition and a method for preparing the same.

BACKGROUND

Polyester (e.g. polyethylene terephthalate (PET)) is widely used in clothing, films, resin molded articles, and the like because of its excellent properties. However, only mature technologies for recycling transparent bottle chips are provided at present, but the total amount of global PET bottles which can be recycled is not enough to meet the requirements in all applications. Therefore, a method for recycling high impurity content coloring bottles, sheet and polyester fabric has become more important to fill the gap in the source of recycled materials.

For a recycled polyester material source, the raw material monomer (such as bis (2-hydroxyethyl) terephthalate (BHET)) can be formed by alcoholysis of the polyester, and the regenerated raw material monomer is subjected to polycondensation reaction again to produce a new polyester. However, the type and content of impurities play a key role in the subsequent polycondensation reaction and the applicability of the obtained polyester.

Accordingly, a composition of bis(2-hydroxyethyl) terephthalate with low impurity content and high thermal stability is needed to solve the above problems.

SUMMARY

According to embodiments of the disclosure, the disclosure provides a method for preparing a composition, such as a composition including bis(2-hydroxyethyl) terephthalate (BHET). The method for preparing a composition includes following steps. A polyethylene terephthalate (PET) waste is provided. The polyethylene terephthalate (PET) waste is subjected to a depolymerization in the presence of a catalyst and an alcoholysis agent to obtain a mixture, wherein an oxidizing atmosphere is continuously introduced into the depolymerization. The mixture is subjected to a solid-liquid separation to obtain a solid. The solid is subjected to a recrystallization treatment to obtain the composition.

According to embodiments of the disclosure, the disclosure also provides a composition, wherein the composition is used for preparing polyethylene terephthalate (PET). The composition includes 99.5 wt % to 99.997 wt % of a compound, 0.001 wt % to 0.25 wt % of mono(2-hydroxyethyl) terephthalate (MHET), and 0.001 wt % to 0.25 wt % of 2-hydroxyethyl[2-(2-hydroxyethoxy)ethyl]terephthalate, based on the weight of the composition. The compound is bis(2-hydroxyethyl) terephthalate (BHET), or a combination of bis(2-hydroxyethyl) terephthalate (BHET) and bis(2-hydroxyethyl) terephthalate oligomer.

A detailed description is given in the following embodiments.

BRIEF DESCRIPTION OF THE DRAWINGS

FIGURE is a flow chart illustrating the method for preparing a composition according to an embodiment of the disclosure.

DETAILED DESCRIPTION

The composition and a method for preparing the same are described in detail in the following description. It will be apparent, however, that the exemplary embodiments set forth herein are used merely for the purpose of illustration, and the inventive concept may be embodied in various forms without being limited to those exemplary embodiments. As used herein, the term "about" in quantitative terms refers to plus or minus an amount that is general and reasonable to persons skilled in the art.

The disclosure provides a composition and the method for preparing a composition. According to embodiments of the disclosure, the composition may be a composition including bis(2-hydroxyethyl) terephthalate (BHET) which is prepared by subjecting a polyethylene terephthalate (PET) waste to a depolymerization and purification, wherein the composition has impurities (i.e. components other than bis(2-hydroxyethyl) terephthalate (BHET) and bis(2-hydroxyethyl) terephthalate oligomer, such as mono(2-hydroxyethyl) terephthalate (MHET), or 2-hydroxyethyl[2-(2-hydroxyethoxy)ethyl]terephthalate) with an extremely low amount. Therefore, it is suitable to prepare polyethylene terephthalate (PET) with improved thermal properties (such as higher glass transition temperature (Tg) and higher melting temperature (Tm)). According to embodiments of the disclosure, the polyethylene terephthalate (PET) prepared by the method of the disclosure has a glass transition temperature (Tg) of 84° C. to 88° C. and a melting temperature (Tm) of 258° C. to 262° C.

According to embodiments of the disclosure, the method for preparing a composition of the disclosure may be used to recycle polyester waste. By means of the method of the disclosure, the bis(2-hydroxyethyl) terephthalate (BHET) composition with high purity may be obtained. In the raw material monomer-containing composition obtained by recycling polyester waste, the residue of key impurities (including partial hydrolysis product (such as mono(2-hydroxyethyl) terephthalate (MHET)) and ether derivative (such as 2-hydroxyethyl[2-(2-hydroxyethoxy)ethyl]terephthalate) directly affects the quality and properties (such as thermal properties and processability) of polyester prepared by the aforementioned composition. However, in the conventional depolymerization process of polyester, it is difficult to reduce the residual amount of key impurities. When the residual amount of the key impurities is not further reduced, the application potentials of the recycled polyester would be greatly limited.

Due to the combination of the specific catalyst and the introduction of the oxidizing atmosphere with specific flow rate, the method for preparing composition of the disclosure can prevent bis (2-hydroxyethyl) terephthalate (BHET) from reacting with an alcoholysis agent to undergo a dehydration reaction, thereby inhibiting the formation of key impurities (such as mono(2-hydroxyethyl) terephthalate (MHET) or 2-hydroxyethyl[2-(2-hydroxyethoxy)ethyl]terephthalate) and reducing impurity residue.

According to embodiments of the disclosure, the disclosure provides a composition (i.e. composition including bis(2-hydroxyethyl) terephthalate) for preparing PET with improved properties (such as thermal properties and mechanical strength). Further, the disclosure provides a method for preparing the aforementioned composition. In addition, the method for preparing composition of the disclosure employing the polyester waste as raw material. Therefore, the purpose for recycling polyester (such as polyethylene terephthalate) can be achieved without limiting the subsequent applications of the recycled polyester.

According to embodiments of the disclosure, as shown in FIGURE, the method for preparing composition of the disclosure 100 can include following steps. First, a polyethylene terephthalate (PET) waste is provided (steps 10). Next, the polyethylene terephthalate (PET) waste is subjected to a depolymerization to obtain a mixture, wherein an oxidizing atmosphere is continuously introduced into the depolymerization (steps 12). According to embodiments of the disclosure, the depolymerization can be performed in the presence of a catalyst and an alcoholysis agent, in order to depolymerize the polyethylene terephthalate (PET) waste to obtain the mixture. In this step, the ratio of the flow rate of the oxidizing atmosphere introducing into the depolymerization to the weight of the polyethylene terephthalate (PET) waste is within a specific range. As a result, the formation of impurities can be effectively inhibited in the system combining oxidizing atmosphere and catalyst via the milder oxidation procedure. Next, the mixture is subjected to a solid-liquid separation to obtain a solid (steps 14). Finally, the solid is subjected to a purification to obtain the composition of the disclosure (steps 16).

According to embodiments of the disclosure, the polyethylene terephthalate (PET) waste may be colorized or uncolorized polyethylene terephthalate waste, such as polyethylene terephthalate bottle sheet, polyethylene terephthalate fabric, polyethylene terephthalate film, or a combination thereof. According to embodiments of the disclosure, the polyethylene terephthalate waste may be subjected to a shredding treatment at first to obtain the polyethylene terephthalate waste with smaller size.

According to embodiments of the disclosure, the alcoholysis agent may be dihydric alcohol, such as monoethylene glycol (MEG), diethylene glycol, propylene glycol, butylene glycol, or a combination thereof. According to embodiments of the disclosure, the amount of the alcoholysis agent is not limited and can be optionally modified by a person of ordinary skill in the field, in order to facilitate the polyethylene terephthalate (PET) waste converting to the raw material monomer. According to embodiments of the disclosure, the weight ratio of the alcoholysis agent to the polyethylene terephthalate (PET) waste may be about 1:1 to 10:1, such as 2:1, 3:1, 4:1, 5:1, 6:1, 7:1, 8:1, or 9:1.

According to embodiments of the disclosure, in order to inhibit the formation of impurities, the depolymerization is performed in the presence of the catalyst during the introduction of oxidizing atmosphere. According to embodiments of the disclosure, the catalyst of the disclosure may be specific metal derived catalyst.

According to embodiments of the disclosure, the catalyst of the disclosure can include metal oxide, metal hydroxide, metal alkoxide, metal organic acid salt, metal carbonate, or a combination thereof. According to embodiments of the disclosure, the catalyst of the disclosure may include lithium oxide, lithium hydroxide, lithium acetate, lithium carbonate, sodium oxide, sodium hydroxide, sodium acetate, sodium carbonate, potassium oxide, potassium hydroxide, potassium acetate, magnesium oxide, magnesium hydroxide, magnesium acetate, carbonic acid Magnesium, calcium oxide, calcium hydroxide, calcium acetate, calcium carbonate, titanium oxide, titanium hydroxide, titanium acetate, titanium carbonate, zinc oxide, zinc hydroxide, zinc acetate, zinc carbonate, manganese oxide, manganese hydroxide, manganese acetate, manganese carbonate, tin acetate, antimony oxide, sodium methoxide, sodium ethoxide, potassium methoxide, potassium ethoxide, or a combination thereof. According to embodiments of the disclosure, the amount of the catalyst is not limited and can be optionally modified by a person of ordinary skill in the field. According to embodiments of the disclosure, the weight ratio of the catalyst to the polyethylene terephthalate (PET) waste may be about 1:1000 to 1:10, such as 1:500, 1:100, 1:50, 1:30, 1:25, 1:20 or 1:15.

According to embodiments of the disclosure, the ratio of the flow rate of the oxidizing atmosphere introduced into the depolymerization to the weight of the polyester waste (such as polyethylene terephthalate waste) and the alcoholysis agent is 100 sccm/Kg to 3,000 sccm/Kg (such as 200 sccm/Kg, 300 sccm/Kg, 400 sccm/Kg, 500 sccm/Kg, 600 sccm/Kg, 700 sccm/Kg, 800 sccm/Kg, 900 sccm/Kg, 1,000 sccm/Kg, 1,500 sccm/Kg, 2,000 sccm/Kg, 2,500 sccm/Kg, or 2,800 sccm/Kg), in order to improve the performance of the subsequent recrystallization treatment and greatly reduce the amounts of impurities.

According to embodiments of the disclosure, when the ratio of the flow rate of the oxidizing atmosphere introduced into the depolymerization to the weight of the polyester waste is too low, the formation of impurities is not effectively inhibited. In addition, when the ratio of the flow rate of the oxidizing atmosphere introduced into the depolymerization to the weight of the polyester waste is too high, the loss of alcoholysis agent is increased.

According to embodiments of the disclosure, the oxidizing atmosphere includes oxygen, ozone, or a combination thereof. According to embodiments of the disclosure, the oxidizing atmosphere can further include an inert gas, wherein the inert gas may be argon, nitrogen, helium or a combination thereof. According to embodiments of the disclosure, in the oxidizing atmosphere, the amount of oxygen (and/or ozone) may be about 5 vol % to 100 vol % (such as 10 vol %, 20 vol %, 30 vol %, 40 vol %, 50 vol %, 60 vol %, 70 vol %, 80 vol %, or 90 vol %) based on the volume of the oxidizing atmosphere. According to embodiments of the disclosure, the oxidizing atmosphere may be air.

According to embodiments of the disclosure, the temperature of the depolymerization may be controlled in a range from 140° C. to 240° C., such as 150° C., 160° C., 170° C., 180° C., 190° C., 200° C., 210° C., 220° C., or 230° C. According to embodiments of the disclosure, at the suitable temperature, the depolymerization rate of polyester is moderate. When the temperature of the depolymerization is too low, the depolymerization rate of polyester would be reduced. When the temperature of the depolymerization is too high, the reaction complexity is increased, thereby facilitating the formation of impurities. According to embodiments of the disclosure, the depolymerization process has a time period of 0.5 hour to 8 hours, such as 1 hour, 2 hours, 3 hours, 4 hours, 5 hours, 6 hours, or 7 hours.

According to embodiments of the disclosure, the solid-liquid separation can be performed via a gravitational separator or a filter separator to separate the solid form the mixture. According to embodiments of the disclosure, the solid-liquid separation has a temperature of 1° C. to 80° C. (such as 5° C., 10° C., 15° C., 20° C., 30° C., 40° C., 50° C., 60° C. or 70° C.). According to embodiments of the disclosure, the purification can include a recrystallization treatment. In the recrystallization treatment, the solid is added into a solvent and the result is heated to a first temperature to force the solid dissolving in the solvent, obtaining a solution. Next, the solution is cooled down to a second temperature. After the completion of recrystallization, the result is subjected to a filtration, and the raw material monomer-containing composition is collected. According to embodiments of the disclosure, the solvent may be water, dichloroethane, ethanol, hexanol, 2-ethyl hexanol, ethyl acetate, butyl acetate or a combination thereof; the first temperature may be 30° C. to 90° C. (such as 50° C., 60° C., 70° C., or 80° C.); and the second temperature may be 1° C. to 25° C. (such as 5° C., 10° C., 15° C., or 20° C.).

According to embodiments of the disclosure, the purification can further include an adsorption treatment. According to embodiments of the disclosure, the solid obtained from the solid-liquid separation is subjected to the adsorption treatment and then subjected to the recrystallization treatment.

According to embodiments of the disclosure, the solid obtained from the solid-liquid separation is subjected to the recrystallization treatment and then subjected to the adsorption treatment.

According to embodiments of the disclosure, the solid obtained from the solid-liquid separation is subjected to the first recrystallization treatment, the adsorption treatment, and the second recrystallization treatment sequentially.

According to embodiments of the disclosure, the purification does not include molecular distillation or supercritical carbon dioxide extraction method in order to reduce the cost and time of the purification.

According to embodiments of the disclosure, the purification can include following steps. The solid is dissolved in a solvent, obtaining a first solution. Next, an adsorbent is added into the first solution. After stirring, the result is filtered, obtaining a second solution. Next, the second solution is subjected to at least one recrystallization treatment, obtaining the raw material monomer-containing composition.

According to embodiments of the disclosure, the adsorbent is not limited and can be optionally modified by a person of ordinary skill in the field, such as zeolite, activated carbon, ion exchange resin, diatomite, aluminum oxide, or a combination thereof.

According to embodiments of the disclosure, in order to enhance the removal efficiency of the pigment and/or dye, before performing the method for preparing composition of the disclosure, the polyester waste may be subjected to a pretreatment via a solvent in order to remove the pigment and/or dye in the polyester waste. According to embodiments of the disclosure, the solution may be aromatic solvent, alcohol solvent, ether solvent, ester solvent, or a combination thereof. For example, the solvent may be mono-ethylene glycol, methylpyrrolidone (NMP), dimethyl sulfoxide (DMSO), cyrene, xylene, propylene glycol methyl ether (PGME), methyl benzoate, ethyl benzoate, benzyl alcohol, or a combination thereof. According to embodiments of the disclosure, the temperature of the pretreatment may be about 100° C. to 180° C., such as 120° C., 130° C., 140° C., 150° C., 160° C., or 170° C.

The disclosure also provides a composition which is obtained by subjecting the polyester waste (such as polyethylene terephthalate waste) to the depolymerization and purification. The composition may be a composition including bis(2-hydroxyethyl) terephthalate (BHET). According to embodiments of the disclosure, the composition has extremely high purity of bis(2-hydroxyethyl) terephthalate (BHET). Namely, in the composition, the total amount of bis(2-hydroxyethyl) terephthalate (BHET) and bis(2-hydroxyethyl) terephthalate oligomer may be greater than or equal to 99.5 wt %, and the total amount of the key impurities (such as the partial hydrolysis product and ether derivative) may be less than or equal to 0.5 wt %, based on the weight of the composition. Herein, the bis(2-hydroxyethyl) terephthalate oligomer may have a structure represented by

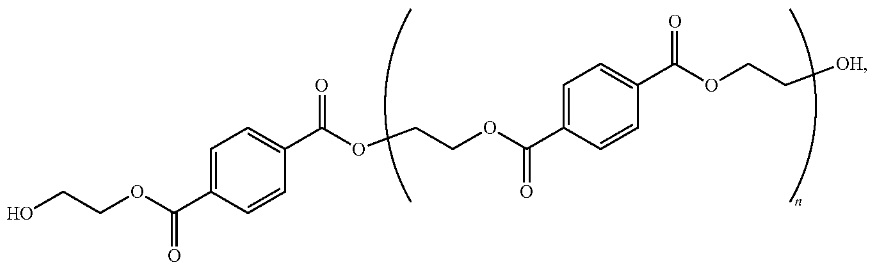

wherein n is 1, 2, or 3. According to embodiments of the disclosure, the composition of the disclosure can include about 99.5 wt % to 99.997 wt % (such as 99.52 wt %, 99.55 wt %, 99.6 wt %, 99.65 wt %, 99.7 wt %, 99.75 wt %, 99.8 wt %, 99.85 wt %, 99.9 wt %, or 99.95 wt %) of a compound, wherein the compound is bis(2-hydroxyethyl) terephthalate (BHET), or a combination of bis(2-hydroxyethyl) terephthalate (BHET) and bis(2-hydroxyethyl) terephthalate oligomer; 0.001 wt % to 0.25 wt % (such as 0.002 wt %, 0.005 wt %, 0.01 wt %, 0.02 wt %, 0.05 wt %, 0.08 wt %, 0.1 wt %, 0.2 wt %, or 0.23 wt %) of mono(2-hydroxyethyl) terephthalate (MHET); and 0.001 wt % to 0.25 wt % (such as 0.002 wt %, 0.005 wt %, 0.01 wt %, 0.02 wt %, 0.05 wt %, 0.08 wt %, 0.1 wt %, 0.2 wt %, or 0.23 wt %) of 2-hydroxyethyl[2-(2-hydroxyethoxy)ethyl]terephthalate, based on the weight of the composition.

According to embodiments of the disclosure, the amount of the components in the composition can be determined by high performance liquid chromatography (HPLC) (with acetonitrile and water serving as mobile phase, wherein the volume ratio of acetonitrile to water may be 1:1). According to embodiments of the disclosure, the compound may be bis(2-hydroxyethyl) terephthalate (BHET), or a combination of bis(2-hydroxyethyl) terephthalate (BHET) and bis(2-hydroxyethyl) terephthalate oligomer.

According to embodiments of the disclosure, when the compound is the combination of bis(2-hydroxyethyl) terephthalate (BHET) and bis(2-hydroxyethyl) terephthalate oligomer, the amount of bis(2-hydroxyethyl) terephthalate (BHET) may be about 97 wt % to 99.897 wt % (such as 97.5 wt %, 98 wt %, 98.5 wt %, 99 wt %, or 99.5 wt %), and the amount of bis(2-hydroxyethyl) terephthalate oligomer may be about 0.1 wt % to 2.45 wt % (such as 0.5 wt %, 1 wt %, 1.5 wt %, 2 wt %, or 2.2 wt %), based on the weight of the composition.

According to some embodiments of the disclosure, since the polyester waste is subjected to the depolymerization in the system combining oxidizing atmosphere and catalyst according to the method of the disclosure, it may be unavoidable that a trace amount of catalyst remains in the composition of the disclosure.

According to embodiments of the disclosure, the composition can further include 0.00001 wt % to 0.003 wt % (0.00002 wt %, 0.00005 wt %, 0.0001 wt %, 0.0005 wt %, 0.001 wt %, or 0.002 wt %) of catalyst, based on the weight of the composition. According to embodiments of the disclosure, the amount of the catalyst that remained in the composition can be determined by inductively coupled plasma mass spectrometry (ICP-MS).

According to embodiments of the disclosure, the catalyst of the disclosure can include metal oxide, metal hydroxide, metal alkoxide, metal organic acid salt, metal carbonate, or a combination thereof. According to embodiments of the disclosure, the catalyst of the disclosure can include lithium oxide, lithium hydroxide, lithium acetate, lithium carbonate, sodium oxide, sodium hydroxide, sodium acetate, sodium carbonate, potassium oxide, potassium hydroxide, potassium acetate, magnesium oxide, magnesium hydroxide, magnesium acetate, carbonic acid Magnesium, calcium oxide, calcium hydroxide, calcium acetate, calcium carbonate, titanium oxide, titanium hydroxide, titanium acetate, titanium carbonate, zinc oxide, zinc hydroxide, zinc acetate, zinc carbonate, manganese oxide, manganese hydroxide, manganese acetate, manganese carbonate, tin acetate, antimony oxide, sodium methoxide, sodium ethoxide, potassium methoxide, potassium ethoxide, or a combination thereof.

According to embodiments of the disclosure, the composition of the disclosure may be prepared by the method for preparing composition of the disclosure 100. Namely, the composition of the disclosure may be prepared by subjecting the polyethylene terephthalate waste to the depolymerization and purification of the disclosure. According to embodiments of the disclosure, due to the extremely low amount of impurities, the composition of the disclosure is suitable for subsequently preparing polyethylene terephthalate (PET) with better thermal properties (such as higher glass transition temperature (Tg) and higher melting temperature (Tm)).

Below, exemplary embodiments will be described in detail so as to be easily realized by a person having ordinary knowledge in the art. The inventive concept may be embodied in various forms without being limited to the exemplary embodiments set forth herein.

EXAMPLES

Preparation of Composition Including Bis(2-Hydroxyethyl) Terephthalate (BHET)

Example 1

100 g of colorized PET bottle sheets, 600 g of monoethylene glycol (MEG), and 2 g of zinc oxide were disposed in a reactor, and the mixture was subjected to a depolymerization at a temperature of 196° C. under one atmospheric pressure. During the depolymerization, air was continuously introduced into the reactor, wherein the flow rate of air was about 140 sccm, and the ratio of the flow rate of air to the weight of colorized PET bottle sheets and MEG was about 200 sccm/Kg. After reacting for 3 hours, the result was filtered, and the filtered cake was collected. Next, the filtered cake was disposed in a recrystallization device and subjected to a recrystallization (with a cooling temperature of 10° C.) with water (having a temperature of 4° C.). Next, the solid obtained from the recrystallization with a solid ratio about 60% was mixed with water, obtaining a solution (with a solid content of about 15 wt %). Next, the solution was heated to 80° C., and 5 g of active carbon (purchase from Sigma-Aldrich) was added into the solution as an adsorbent. After stirring for 30 minutes, the result was filtered and then the obtained filtered cake was disposed in the recrystallization device and subjected to a recrystallization (with a cooling temperature of 10° C.) with water (having a temperature of 4° C.). Finally, the result of recrystallization was dried at 80° C. under vacuum, obtaining Composition (1).

The amount of the components in Composition (1) was determined by high performance liquid chromatography (HPLC) (with acetonitrile and water serving as mobile phase, wherein the volume ratio of acetonitrile to water was 1:1), the amount of Zn that remained in Composition (1) was determined by inductively coupled plasma mass spectrometry (ICP-MS), and the results are shown in Table 1.

Example 2

Example 2 was performed in the same manner as in Example 1 except that the flow rate of air introduced into the reactor was reduced such that the ratio of the flow rate of air to the weight of colorized PET bottle sheets and MEG was reduced from about 200 sccm/Kg to 100 sccm/Kg, obtaining Composition (2).

The amount of the components in Composition (2) was determined by high performance liquid chromatography (HPLC) (with acetonitrile and water serving as mobile phase, wherein the volume ratio of acetonitrile to water was 1:1), the amount of Zn that remained in Composition (2) was determined by inductively coupled plasma mass spectrometry (ICP-MS), and the results are shown in Table 1.

Example 3

Example 3 was performed in the same manner as in Example 1 except that the colorized PET bottle sheets was replaced with the PET fabric, zinc oxide was replaced with zinc acetate, and the flow rate of air introduced into the reactor was increased such that the ratio of the flow rate of air to the weight of colorized PET bottle sheets and MEG was increased from about 200 sccm/Kg to 1,600 sccm/Kg, obtaining Composition (3).

The amount of the components in Composition (3) was determined by high performance liquid chromatography (HPLC) (with acetonitrile and water serving as mobile phase, wherein the volume ratio of acetonitrile to water was 1:1), the amount of Zn that remained in Composition (3) was determined by inductively coupled plasma mass spectrometry (ICP-MS), and the results are shown in Table 1.

Example 4

Example 4 was performed in the same manner as in Example 1 except that the colorized PET bottle sheets was replaced with the PET fabric, zinc oxide was replaced with zinc acetate, the air was replaced by oxygen and the flow rate of oxygen introduced into the reactor was reduced such that the ratio of the flow rate of oxygen to the weight of colorized PET bottle sheets and MEG was reduced from about 200 sccm/Kg to 150 sccm/Kg, obtaining Composition (4).

The amount of the components in Composition (4) was determined by high performance liquid chromatography (HPLC) (with acetonitrile and water serving as mobile phase, wherein the volume ratio of acetonitrile to water was 1:1), the amount of Zn that remained in Composition (4) was determined by inductively coupled plasma mass spectrometry (ICP-MS), and the results are shown in Table 1.

Example 5

Example 5 was performed in the same manner as in Example 1 except that the colorized PET bottle sheets was replaced with the PET fabric, the amount of mono-ethylene glycol (MEG) was increased from 600 g to 800 g, and the flow rate of air introduced into the reactor was increased such that the ratio of the flow rate of air to the weight of colorized PET bottle sheets and MEG was increased from about 200 sccm/Kg to 1000 ccm/Kg, obtaining Composition (5).

The amount of the components in Composition (5) was determined by high performance liquid chromatography (HPLC) (with acetonitrile and water serving as mobile phase, wherein the volume ratio of acetonitrile to water was 1:1), the amount of Zn that remained in Composition (5) was determined by inductively coupled plasma mass spectrometry (ICP-MS), and the results are shown in Table 1.

Example 6

100 g of PET fabric, 800 g of mono-ethylene glycol (MEG), and 2 g of zinc acetate were disposed in a reactor, and the mixture was subjected to the depolymerization at 196° C. under one atmospheric pressure. During the depolymerization, the air doped with ozone (with an ozone concentration of 30 ppm) was introduced into the reactor, wherein the flow rate of air doped with ozone was about 140 sccm, and the ratio of the flow rate of air doped with ozone to the weight of colorized PET bottle sheets and MEG was about 200 sccm/Kg. After reacting for 3 hours, the result was filtered, and the filtered cake was collected. Next, the filtered cake was disposed in a recrystallization device and subjected to a recrystallization (with a cooling temperature of 10° C.) with water (having a temperature of 80° C.). Next, the solid obtained from the recrystallization was mixed with water, obtaining a solution (with a solid content of about 10 wt %). Next, the solution was heated to 80° C., and 10 g of active carbon (purchase from Sigma-Aldrich) was added into the solution. After stirring for 30 minutes, the result was filtered and then the obtained filtered cake was disposed in the recrystallization device and subjected to a recrystallization (with a cooling temperature of 10° C.) with water (having a temperature of 80° C.). Finally, the result of recrystallization was dried at 80° C. under vacuum, obtaining Composition (6).

The amount of the components in Composition (6) was determined by high performance liquid chromatography (HPLC) (with acetonitrile and water serving as mobile phase, wherein the volume ratio of acetonitrile to water was 1:1), the amount of Zn that remained in Composition (6) was determined by inductively coupled plasma mass spectrometry (ICP-MS), and the results are shown in Table 1.

TABLE 1

| | bis(2-hydroxyethyl) terephthalate (BHET) (wt %) | bis(2-hydroxyethyl) terephthalate oligomer (wt %) | mono(2-hydroxyethyl) terephthalate (MHET) (wt %) | 2-hydroxyethyl[2-(2-hydroxyethoxy)ethyl]terephthalate (wt %) | zinc (ppm) |
|---|---|---|---|---|---|
| Example 1 | 98.23 | 1.73 | 0.02 | 0.02 | 4.4 |
| Example 2 | 98.01 | 1.80 | 0.16 | 0.03 | 1 |
| Example 3 | 98.33 | 1.63 | 0.02 | 0.02 | 0.2 |
| Example 4 | 97.72 | 2.21 | 0.02 | 0.05 | 1.7 |
| Example 5 | 97.30 | 2.40 | 0.18 | 0.12 | 3.1 |
| Example 6 | 97.49 | 2.10 | 0.20 | 0.21 | 5.7 |

Comparative Example 1

100 g of colorized PET bottle sheets, 600 g of mono-ethylene glycol (MEG), and 2 g of zinc oxide were disposed in a reactor, and the mixture was subjected to the depolymerization at 196° C. under one atmospheric pressure. During the depolymerization, no air was additionally introduced into the reactor. After reacting for 3 hours, the result was filtered, and the filtered cake was collected. Next, the filtered cake was disposed in a recrystallization device and subjected to a recrystallization (with a cooling temperature of 10° C.) with water (having a temperature of 4° C.). Next, the solid obtained from the recrystallization was mixed with water, obtaining a solution (with a solid content of about 15 wt %). Next, the solution was heated to 80° C., and 5 g of active carbon (purchased from Sigma-Aldrich) was added into the solution. After stirring for 30 minutes, the result was filtered and then the obtained filtered cake was disposed in the recrystallization device and subjected to a recrystallization (with a cooling temperature of 10° C.) with water (having a temperature of 4° C.). Finally, the result of recrystallization was dried at 80° C. under vacuum, obtaining Composition (7).

The amount of the components in Composition (7) was determined by high performance liquid chromatography (HPLC) (with acetonitrile and water serving as mobile phase, wherein the volume ratio of acetonitrile to water was 1:1), the amount of Zn that remained in Composition (7) was determined by inductively coupled plasma mass spectrometry (ICP-MS), and the results are shown in Table 2.

Comparative Example 2

Comparative Example 2 was performed in the same manner as in Comparative Example 1 except that the amount of zinc oxide was increased from 2 g to 3 g, obtaining Composition (8).

The amount of the components in Composition (8) was determined by high performance liquid chromatography (HPLC) (with acetonitrile and water serving as mobile phase, wherein the volume ratio of acetonitrile to water was 1:1), the amount of Zn that remained in Composition (8) was determined by inductively coupled plasma mass spectrometry (ICP-MS), and the results are shown in Table 2.

Comparative Example 3

100 g of PET fabric, 600 g of mono-ethylene glycol (MEG), and 2 g of zinc acetate were disposed in a reactor, and the mixture was subjected to the depolymerization at 196° C. under one atmospheric pressure. During the depolymerization, no air was additionally introduced into the reactor. After reacting for 3 hours, the result was filtered, and the filtered cake was collected. Next, the filtered cake was disposed in a recrystallization device and subjected to a recrystallization (with a cooling temperature of 10° C.) with water (having a temperature of 4° C.). Next, the solid obtained from the recrystallization was mixed with water, obtaining a solution (with a solid content of about 15 wt %). Next, the solution was heated to 80° C., and 10 g of active carbon (purchased from Sigma-Aldrich) was added into the solution. After stirring for 30 minutes, the result was filtered and then the obtained filtered cake was disposed in the recrystallization device and subjected to a recrystallization (with a cooling temperature of 10° C.) with water (having a temperature of 4° C.). Finally, the result of recrystallization was dried at 80° C. under vacuum, obtaining Composition (9).

The amount of the components in Composition (9) was determined by high performance liquid chromatography (HPLC) (with acetonitrile and water serving as mobile phase, wherein the volume ratio of acetonitrile to water was 1:1), the amount of Zn that remained in Composition (9) was determined by inductively coupled plasma mass spectrometry (ICP-MS), and the results are shown in Table 2.

Comparative Example 4

Comparative Example 4 was performed in the same manner as in Comparative Example 3 except that the amount of mono-ethylene glycol (MEG) was increased from 600 g to 800 g, and the amount of zinc acetate was increased from 2 g to 3 g, obtaining Composition (10).

The amount of the components in Composition (10) was determined by high performance liquid chromatography (HPLC) (with acetonitrile and water serving as mobile phase, wherein the volume ratio of acetonitrile to water was 1:1), the amount of Zn that remained in Composition (10) was determined by inductively coupled plasma mass spectrometry (ICP-MS), and the results are shown in Table 2.

Comparative Example 5

Comparative Example 5 was performed in the same manner as in Comparative Example 3 except that zinc acetate was replaced with zinc oxide, obtaining Composition (11).

The amount of the components in Composition (11) was determined by high performance liquid chromatography (HPLC) (with acetonitrile and water serving as mobile phase, wherein the volume ratio of acetonitrile to water was 1:1), the amount of Zn that remained in Composition (11) was determined by inductively coupled plasma mass spectrometry (ICP-MS), and the results are shown in Table 2.

Comparative Example 6

The amount of components of the commercial BHET composition (commercially available from JEPLAN) was determined by high performance liquid chromatography (HPLC) (with acetonitrile and water serving as mobile phase, wherein the volume ratio of acetonitrile to water was 1:1), the amount of Zn that remained in the composition was determined by inductively coupled plasma mass spectrometry (ICP-MS), and the results are shown in Table 2.

TABLE 2

| | bis(2-hydroxyethyl) terephthalate (BHET) (wt %) | bis(2-hydroxyethyl) terephthalate oligomer (wt %) | mono(2-hydroxyethyl) terephthalate (MHET) (wt %) | 2-hydroxyethyl[2-(2-hydroxyethoxy)ethyl]terephthalate (wt %) | zinc (ppm) |
|---|---|---|---|---|---|
| Comparative Example 1 | 97.20 | 2.50 | 0.2 | 0.1 | 2.6 |
| Comparative Example 2 | 97.30 | 1.70 | 0.63 | 0.37 | 1.2 |
| Comparative Example 3 | 96.8 | 2.59 | 0.20 | 0.41 | 6.9 |
| Comparative Example 4 | 96.1 | 3.0 | 0.39 | 0.60 | 15 |
| Comparative Example 5 | 97.40 | 2.00 | 0.28 | 0.32 | 34 |
| Comparative Example 6 | 96.70 | 1.70 | 1.1 | 0.50 | 0.3 |

As shown in Table 1, the total amount of bis(2-hydroxyethyl) terephthalate and bis(2-hydroxyethyl) terephthalate oligomer of the compositions prepared by the method of the disclosure is greater than 99.5 wt %. In addition, as shown in Table 1, the amount of mono(2-hydroxyethyl) terephthalate (MHET) and the amount of 2-hydroxyethyl[2-(2-hydroxyethoxy)ethyl]terephthalate in the composition of the disclosure are both less than 0.25 wt %. As shown in Table 2, when subjecting polyester waste (such as colorized polyester waste) to a depolymerization without introduction of oxidizing atmosphere, the total amount of bis(2-hydroxyethyl) terephthalate and bis(2-hydroxyethyl) terephthalate oligomer of the compositions is less than 99.5 wt %. Further, at least one of the amount of mono(2-hydroxyethyl) terephthalate (MHET) and the amount of 2-hydroxyethyl[2-(2-hydroxyethoxy)ethyl]terephthalate in the compositions of Comparative Examples is greater than 0.25 wt %.

Thermal Properties Evaluation of PET Prepared from Compositions

Compositions (1)-(11) and the commercial BHET composition (commercially available from JEPLAN) (50 g) were disposed in a polymerization reactor individually. Next, the polymerization reactor was vacuumed and refilled with nitrogen gas and then the polymerization reactor was heated to 130° C., thereby melting bis(2-hydroxyethyl) terephthalate (and bis(2-hydroxyethyl) terephthalate oligomer). Next, the catalyst (commercially available from AkzoNobel with a trade number of C-94) was added into the polymerization reactor, wherein the amount of the catalyst was 10 ppm (based on the weight of the composition). Next, the polymerization reactor was heated to 197° C. and stood for 60 minutes. Next, the polymerization reactor was heated to 275° C. and the pressure of the polymerization reactor was reduced to less than 1 torr. After standing for 60 minutes, the polymerization reactor was cooled to room temperature, individually obtaining polyethylene terephthalate (1)-(12). The glass transition temperature (Tg) and the melting temperature (Tm) of polyethylene terephthalate (1)-(12) were measured, and the results are shown in Table 3. The glass transition temperature (Tg) and the melting temperature (Tm) are measured by differential scanning calorimeter (DSC) (available from TA Instruments, Inc. under the trade designation of Discovery DSC 25).

TABLE 3

| | composition | glass transition temperature (° C.) | melting temperature (° C.) |
|---|---|---|---|
| Polyethylene terephthalate (1) | Example 1 | 85.4 | 261.5 |
| Polyethylene terephthalate (2) | Example 2 | 85.3 | 260.6 |
| Polyethylene terephthalate (3) | Example 3 | 85.6 | 261.5 |
| Polyethylene terephthalate (4) | Example 4 | 86.9 | 260.3 |
| Polyethylene terephthalate (5) | Example 5 | 87.7 | 259 |
| Polyethylene terephthalate (6) | Example 6 | 85.3 | 259.7 |
| Polyethylene terephthalate (7) | Comparative Example 1 | 79.7 | 256.9 |
| Polyethylene terephthalate (8) | Comparative Example 2 | 77.9 | 252.2 |
| Polyethylene terephthalate (9) | Comparative Example 3 | 77.9 | 252.7 |
| Polyethylene terephthalate (10) | Comparative Example 4 | 78.9 | 256.1 |
| Polyethylene terephthalate (11) | Comparative Example 5 | 78.5 | 252 |
| Polyethylene terephthalate (12) | commercial BHET composition (JEPLAN) | 78.9 | 251.4 |

As shown in Table 3, since the amount of mono(2-hydroxyethyl) terephthalate (MHET) and the amount of 2-hydroxyethyl[2-(2-hydroxyethoxy)ethyl]terephthalate in the compositions (Examples 1-6) of the disclosure are both less than 0.25 wt %, polyethylene terephthalate prepared from the compositions of the disclosure has a glass transition temperature of 85° C. to 88° C. and a melting temperature of 259° C. to 262° C.

In contrast, the total amount of bis(2-hydroxyethyl) terephthalate and bis(2-hydroxyethyl) terephthalate oligomer in the compositions of Comparative Examples 1-6 is less than 99.5 wt % (i.e. the impurities are greater than 0.5 wt %), thereby severely affects the thermal properties (such as glass transition temperature less than 80° C. and melting temperature less than 257° C.) of the obtained polyethylene terephthalate.

Accordingly, due to the combination of the specific catalyst and the introduction of the oxidizing atmosphere with specific flow rate, the method for preparing composition of the disclosure inhibits the formation of key impurities. Therefore, the polyethylene terephthalate prepared from the composition of the disclosure exhibits better thermal properties (such as higher glass transition temperature and higher melting temperature).

It will be clear that various modifications and variations can be made to the disclosed methods and materials. It is intended that the specification and examples be considered as exemplary only, with the true scope of the disclosure being indicated by the following claims and their equivalents.

What is claimed is:

1. A method for preparing a composition, comprising:
providing a polyethylene terephthalate waste;
subjecting the polyethylene terephthalate waste to a depolymerization in the presence of a catalyst and an alcoholysis agent to obtain a mixture, wherein an oxidizing atmosphere is continuously introduced into the depolymerization, and a ratio of a flow rate of the oxidizing atmosphere to a weight of the polyethylene terephthalate waste and the alcoholysis agent is 100 sccm/Kg to 3,000 sccm/Kg;
subjecting the mixture to a solid-liquid separation, obtaining a solid; and
subjecting the solid to a purification, obtaining the composition.

2. The method as claimed in claim 1, wherein the polyethylene terephthalate waste is polyethylene terephthalate bottle sheet, polyethylene terephthalate fabric, polyethylene terephthalate film, or a combination thereof.

3. The method as claimed in claim 1, wherein the catalyst comprises metal oxide, metal hydroxide, metal alkoxide, metal organic acid salt, metal carbonate, or a combination thereof.

4. The method as claimed in claim 1, wherein the catalyst comprises lithium oxide, lithium hydroxide, lithium acetate, lithium carbonate, sodium oxide, sodium hydroxide, sodium acetate, sodium carbonate, potassium oxide, potassium hydroxide, potassium acetate, magnesium oxide, magnesium hydroxide, magnesium acetate, magnesium carbonate, calcium oxide, calcium hydroxide, calcium acetate, calcium carbonate, titanium oxide, titanium hydroxide, titanium acetate, titanium carbonate, zinc oxide, zinc hydroxide, zinc acetate, zinc carbonate, manganese oxide, manganese hydroxide, manganese acetate, manganese carbonate, tin acetate, antimony oxide, sodium methoxide, sodium ethoxide, potassium methoxide, potassium ethoxide, or a combination thereof.

5. The method as claimed in claim 1, wherein the alcoholysis agent is a dihydric alcohol.

6. The method as claimed in claim 1, wherein the alcoholysis agent is mono-ethylene glycol, diethylene glycol, propylene glycol, butylene glycol, or a combination thereof.

7. The method as claimed in claim 1, wherein the oxidizing atmosphere comprises oxygen, ozone, or a combination thereof.

8. The method as claimed in claim 1, wherein the depolymerization has a temperature of 140° C. to 240° C., and the depolymerization has a process time of 0.5 hour to 8 hours.

9. The method as claimed in claim 1, wherein the purification comprises a recrystallization treatment.

10. The method as claimed in claim 9, wherein the purification further comprises an adsorption treatment.

11. A composition, which is prepared by the method as claimed in claim 1, comprising:
97 wt % to 99.897 wt % of bis(2-hydroxyethyl) terephthalate;
0.1 wt % to 2.45 wt % of bis(2-hydroxyethyl) terephthalate oligomer,
wherein a total amount of bis(2-hydroxyethyl) terephthalate and bis(2-hydroxyethyl) terephthalate oligomer is 99.5 wt % to 99.997 wt %;
0.001 wt % to 0.25 wt % of mono(2-hydroxyethyl) terephthalate; and
0.001 wt % to 0.25 wt % of 2-hydroxyethyl[2-(2-hydroxyethoxy)ethy l]terephthalate, based on the weight of the composition.

12. The composition as claimed in claim 11, further comprising:
0.00001 wt % to 0.003 wt % of catalyst, based on the weight of the composition.

* * * * *